(12) United States Patent
Mizutani et al.

(10) Patent No.: US 6,682,515 B1
(45) Date of Patent: Jan. 27, 2004

(54) DISPOSABLE ABSORBENT SANITARY ARTICLE

(75) Inventors: Katsumi Mizutani, Kagawa-ken (JP); Yoshio Ono, Kagawa-ken (JP); Hirotomo Mukai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 160 days.

(21) Appl. No.: 09/715,885

(22) Filed: Nov. 17, 2000

(30) Foreign Application Priority Data

Nov. 19, 1999 (JP) .......................................... 11-330580

(51) Int. Cl.⁷ ................................................. A61F 13/15
(52) U.S. Cl. .............................. 604/385.27; 604/385.28
(58) Field of Search ........................ 604/385.24–385.28

(56) References Cited

U.S. PATENT DOCUMENTS

| | | | | |
|---|---|---|---|---|
| 5,246,431 A | | 9/1993 | Minetola et al. | |
| 5,439,459 A | * | 8/1995 | Tanji et al. | 156/164 |
| 5,669,896 A | * | 9/1997 | Kielpikowski | 604/373 |
| 5,674,215 A | * | 10/1997 | Ronnberg | 156/164 |
| 5,735,838 A | * | 4/1998 | Ronnberg et al. | 604/385.25 |
| 5,746,732 A | * | 5/1998 | Olsson et al. | 604/385.2 |
| 5,993,433 A | * | 11/1999 | St. Louis et al. | 604/385.27 |
| 6,120,486 A | * | 9/2000 | Toyoda et al. | 604/385.2 |

FOREIGN PATENT DOCUMENTS

| | | |
|---|---|---|
| WO | WO 93/09739 | 5/1993 |
| WO | WO 94/18927 | 9/1994 |

* cited by examiner

Primary Examiner—Weilun Lo
Assistant Examiner—C L Anderson
(74) Attorney, Agent, or Firm—Butzel Long

(57) ABSTRACT

A disposable absorbent sanitary article that includes sheets to form a pair of flaps and a pair of flaps. The sheets are folded along flap fold lines back onto themselves, respectively, to form free edge portions of the respective pairs of flaps. Elastic members are secured under tension to the sheets inside the respective free edge portions and are spaced from the fold lines at least by 1 mm, respectively.

5 Claims, 6 Drawing Sheets

DISPOSABLE ABSORBENT SANITARY ARTICLE

BACKGROUND OF THE INVENTION

This invention relates to a disposable absorbent sanitary article for absorbing and retaining body fluids such as disposable diapers or menstruation pads.

The bulletin of WO93/09739 discloses a sanitary article provided with a pair of elasticized side flaps. This article includes a first pair of elasticized side flaps defining transversely opposite side edges of the article and a second pair of elasticized flaps lying on the inner side of the article and normally biased to rise upward on a liquid-absorbent core. A liquid-pervious topsheet and a liquid-impervious backsheet sandwiching the core extend outward beyond transversely opposite side edges of the core. These extensions of the respective sheets are put flat and joined together to form the first side flaps. Distal edges of the side flaps are respectively provided with first elastic members extending under tension longitudinally of the flaps between the top- and backsheets. The second side flaps are formed by placing separately prepared sheets upon the upper surface of the topsheet and folding these sheets in respective two halves and putting them flat together, respectively, along the respective distal edges with second elastic members extending under tension between the respective two halves. These first and second elastic members elastically contract and come in contact with a wearer's skin as the article is put on the wearer's body.

In the case of the article disclosed by the aforesaid bulletin, the distal edges of the first flaps correspond to lines along which the top- and backsheets placed upon each other have been cut to contour the article in conformity with its desired shape and, in other words, the distal edges of the first flaps partially define the article's contour. The first elastic members are placed in the vicinity of the respective distal edges parallel to them and elasticize the respective distal edges. The distal edges of the first flaps, i.e., the cut ends of the top- and backsheets are not rounded and may irritate the wearer's skin as the napkin is put on the wearer's body. In addition, the first elastic members have a secondary effect to increase a rigidity of the distal edges, therefore irritation of the wearer's skin due to the cut ends and eventually to deteriorate a feeling to wear the napkin.

The distal edges of the second side flaps formed by folding the respective sheets so as to wrap the respective second elastic members with such an arrangement, the sheets sometimes cut into the wearer's skin rather than come in contact with the wearer's skin, together with the second elastic members. Thus, the second side flaps also may create a feeling of discomfort against the wearer.

SUMMARY OF THE INVENTION

It is an object of this invention to provide a disposable absorbent sanitary article such as disposable diapers or menstruation pads that are designed to alleviate skin stimulation due to the elasticized side flaps.

According to this invention, there is provided a disposable absorbent sanitary article having a body-side surface and an undergarment-side surface opposed to the body-side surface and comprising a basic structure adapted to absorb and retain body fluids between the two surfaces and a plurality of flaps adapted to be elastically placed against the wearer as the article is put on the wearer.

This invention further comprises any one pair of the plural pairs of flaps each having a transverse direction and a longitudinal direction orthogonal to the transverse direction and formed by a sheet extending outward from the basic structure and an elastic member wrapped by the sheet in a state tensioned in the longitudinal direction, the flap having a proximal edge portion adjacent as viewed in the transverse direction and an elastically stretchable free edge spaced from a top surface of the basic structure, the flap is folded in the free edge portion along a fold line extending in the longitudinal direction back onto itself with the elastic member inside and wherein the elastic member is placed at least 1 mm apart from the fold line toward the proximal edge portion and secured to the inner surface of the sheet.

In the disposable absorbent sanitary article according to this invention the sheet forming each of the flaps is folded back along the line to define the free edge portion of the flap and joined to itself so that the free edge portion may present an annular cross-section and the elastic member elasticizing this flap is spaced from the line toward the proximal edge portion of the flap at least by 1 mm. Such a unique arrangement enables the annular free edge portion of the flap to be deformed and thereby to offer an cushioning effect. In this way, there is no apprehension that the elastic member might cut into the wearer's skin and create a feeling of discomfort against the wearer.

DETAILED DESCRIPTION OF THE PREFERRED EMBODIMENTS

Details of a disposable absorbent sanitary article according to this invention will be more fully understood from the description given hereunder with reference to the accompanying drawings.

Figure 1:
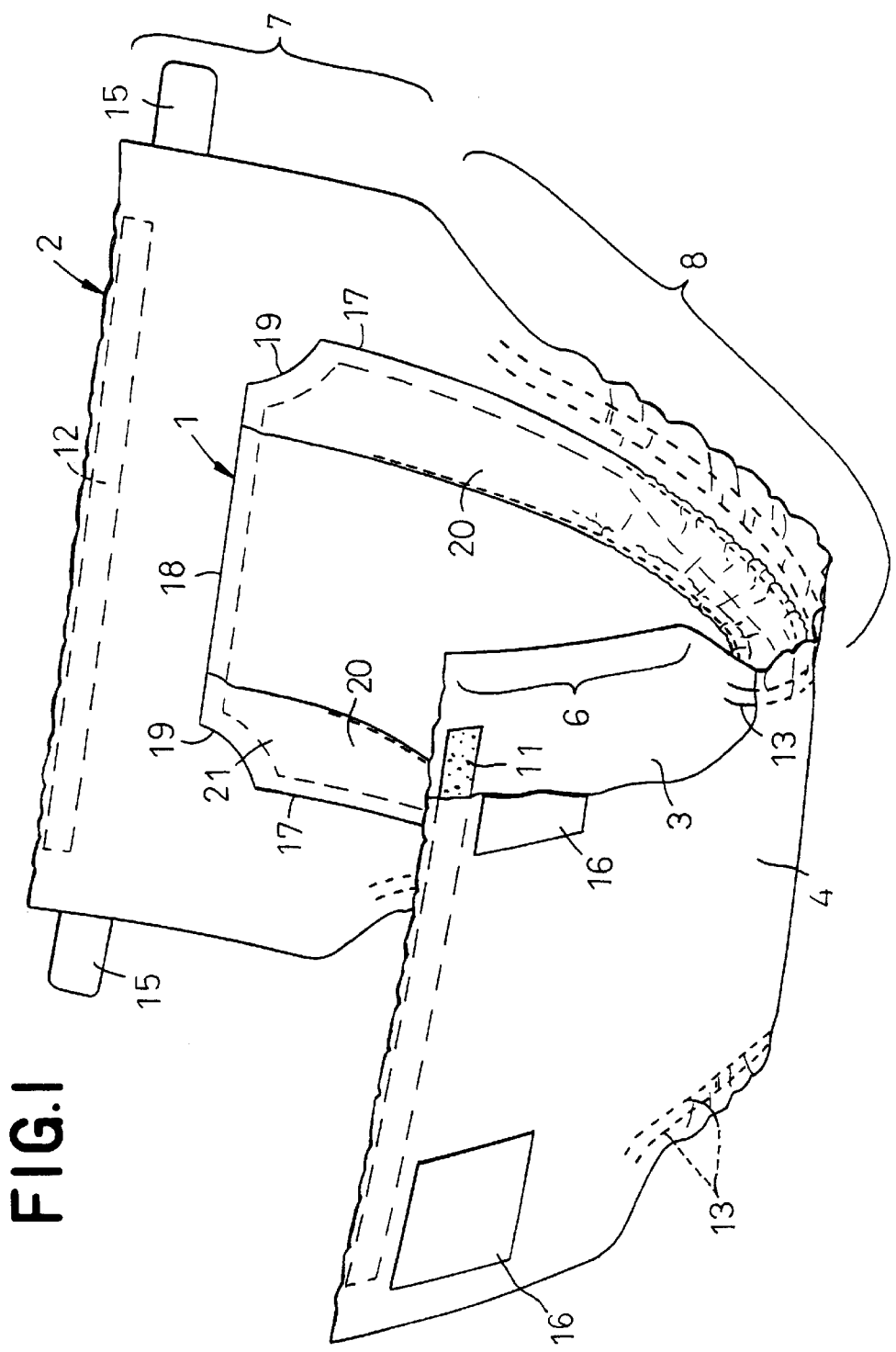
FIG. 1 is a perspective view depicting a diaper cover to which a disposable absorbent sanitary article of this invention is attached.

FIG. 1 depicts a urine pad 1 as one embodiment of a disposable absorbent sanitary article attached to a diaper cover 2 as a specific embodiment of the garment. The diaper cover 2 comprises an inner sheet 3 made of a nonwoven fabric and an outer sheet 4 made of a plastic film placed upon the inner sheet 3 to define a front waist region 6, a rear waist region 7 and a crotch region 8 extending between these two waist regions 6, 7. Front and rear terminal edges of the front and rear waist regions 6, 7, respectively, are provided with waist-hole elastic members 11, 12 circumferentially extending between the inner and outer sheets 3, 4 and secured under tension to the inner surface of at least one of the inner and outer sheets 3, 4. Along transversely opposite side edges of the crotch region 8, leg-hole elastic members 13 extend between the inner and outer sheets 3, 4 and secured under tension to the inner surface of at least one of these inner and outer sheets 3, 4. The rear waist region 7 is provided with a pair of tape fasteners 15 extending outward from transversely opposite side edges of the waist region 7, respectively. Each of the fasteners 15 is a hook member adapted to cooperate with a loop member to complete a mechanical fastening system. Being adopted for the diaper cover 2, the hook members 15 are anchored on the loop member attached to the outer sheet 4 of the front waist region 6 in the form of a strip of target tape 16.

The urine pad 1 is detachably attached to the inner side of the diaper cover 2 and contoured by a pair of transversely opposite side edges extending longitudinally as viewed in FIG. 1 parallel to each other across the crotch region 8 into the front and rear waist regions 6, 7, a pair of front and rear terminal edges 18 circumferentially extending parallel to each other (See FIG. 2 also) and four oblique edges 19 each extending between a pair of adjacent ends of the front or rear terminal edge 18 and the associated side edge 17 to define each corner 21 of the pad 1. Spaced from the respective side edges 17, a pair of barrier flaps 20, 20 extending between the pair of terminal edges 18, 18 parallel to the side edges 17.

Figure 2:
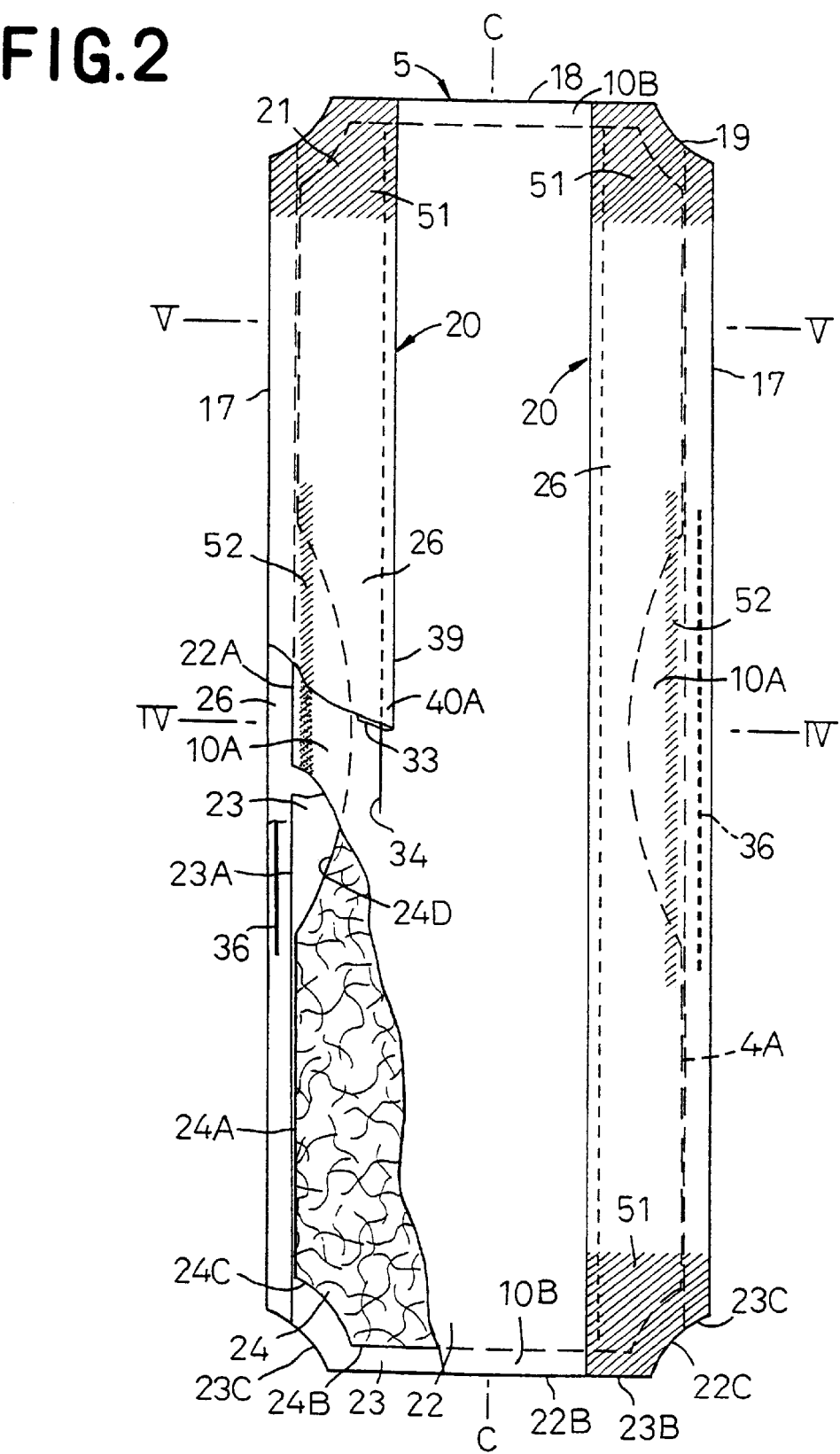
FIG. 2 is a front view depicting the partially cutaway disposable absorbent sanitary article.
Figure 3:
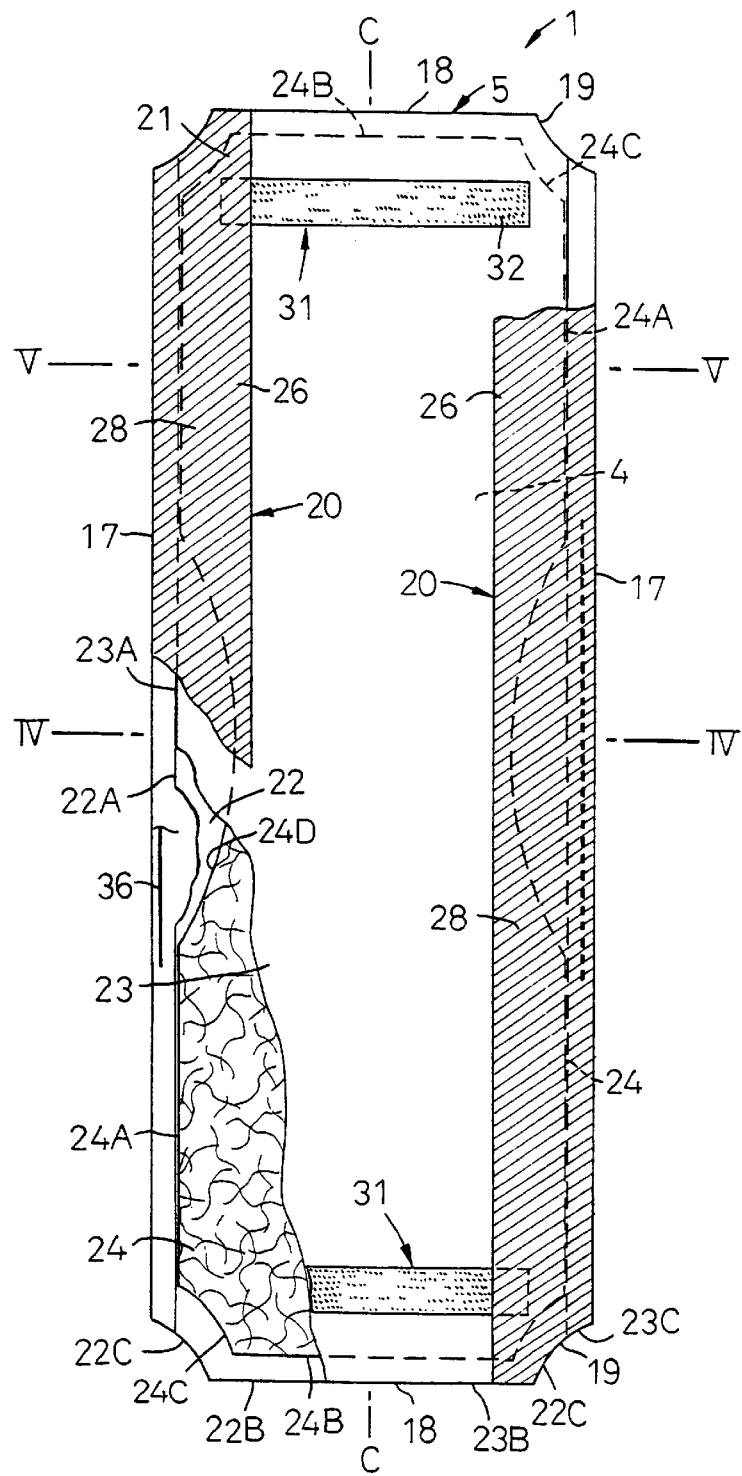
FIG. 3 is a rear view depicting the partially cutaway absorbent sanitary article.
Figure 4:
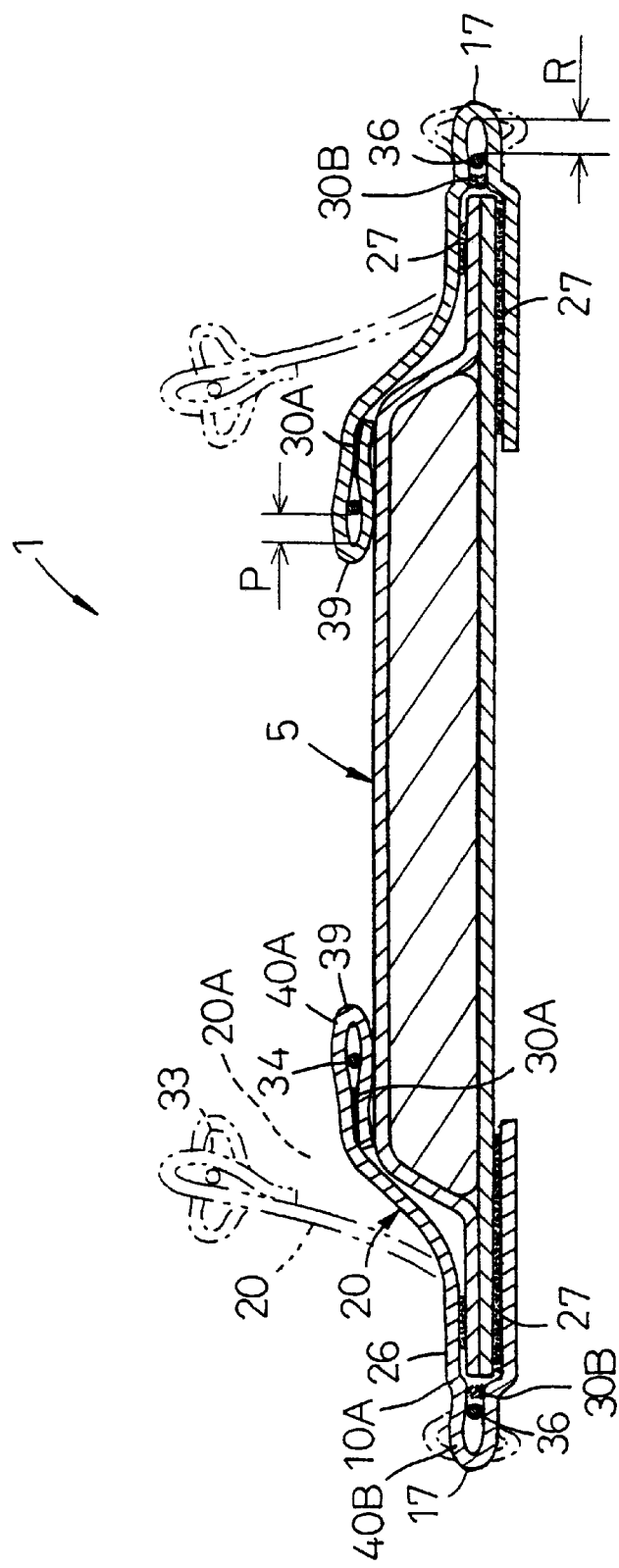
FIG. 4 is a sectional view taken along line IV—IV in FIG. 2.
Figure 5:
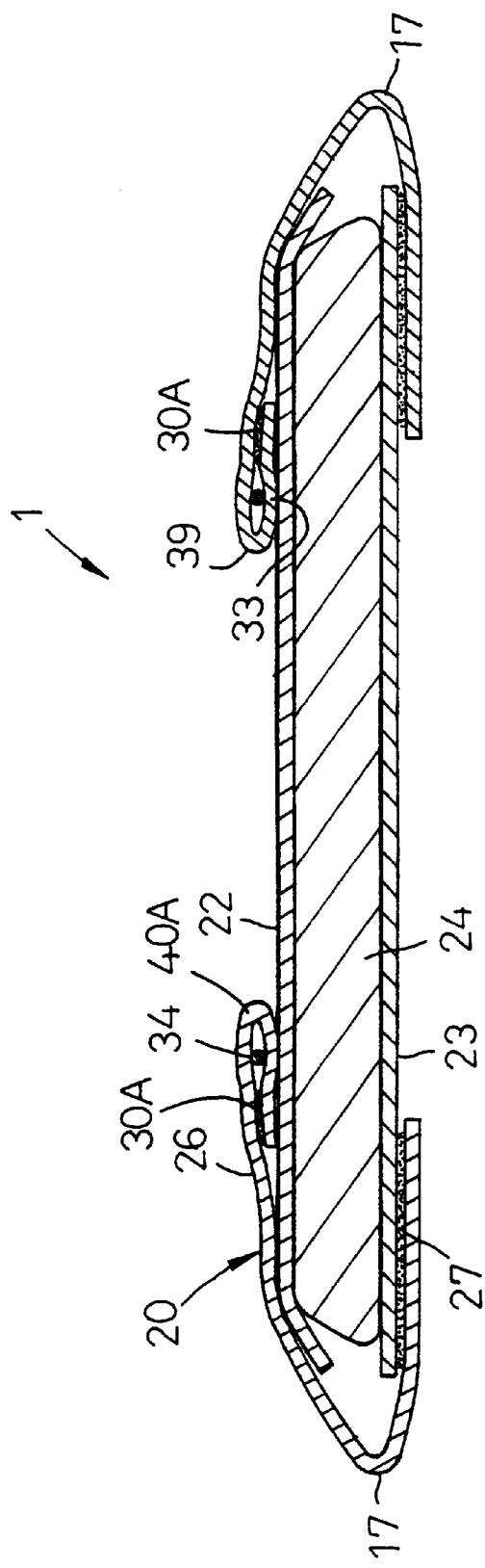
FIG. 5 is a sectional view taken along line V—V in FIG. 2.

FIGS. 2 and 3 are respectively front and rear view depicting the disposable absorbent sanitary article as detached from the diaper cover 2. FIG. 4 is a sectional view taken along line IV—IV bisecting a length of the pad 1 and FIG. 5 is a sectional view taken along line V—V in FIG. 2. The pad 1 has a basic structure 5 comprising a liquid-pervious topsheet 22 to come in contact with the wearer's skin, a liquid-impervious backsheet 23 opposed to the topsheet 22 and a body fluid absorbent core 24 disposed between these two sheets 22, 23. The pad 1 is shaped symmetrically about a center line C—C extending longitudinally to bisect a width of the pad 1.

The core 24 is contoured by a pair of transversely opposite side edges 24A extending longitudinally parallel to each other, a pair of longitudinally opposite terminal edges 24B extending transversely parallel to each other and oblique edges 24C each extending between a pair of adjacent ends of the terminal edge 24B and the associated side edge 24A. Such oblique edges 24C slightly curves inwardly of the core 24 so as to reduce a width of the core 24. The side edges 24A curve at their longitudinally middle zones so that the core 24 as a whole may present an hourglass-shape.

The topsheet 22 is contoured by transversely opposite rectilinear side edges 22A extending longitudinally along the respective side edges 24A of the core 24, longitudinally opposite terminal edges 22B extending transversely and oblique edges 22C defined at the respective corners 21 of the pad 1, each oblique edge 22c extending to describe a gentle curve between each pair of adjacent ends of the side edge 22A and the associated terminal edge 22B.

The backsheet 23 is substantially identical to the topsheet 22 in shape as well as in size and contoured by transversely opposite rectilinear side edges 23A extending longitudinally along the respective side edges 24A of the core 24, longitudinally opposite terminal edges 23B extending transversely and oblique edges 23C defined at the respective corners 21 of the pad 1, each oblique edge 23c extending to describe a gentle curve between each pair of adjacent ends of the side edge 23A and the associated terminal edge 23B. The top- and backsheets 22, 23 extend outward beyond curved regions 24D of the respective side edges 24A, the longitudinally opposite terminal ends 24B and the oblique edges 24C of the core 24. The top- and backsheets 22, 23 are placed upon and joined to each other over these extensions by means of hot melt adhesive (not shown) to form a pair of side flaps 10A laterally extending from the basic structure 5 and a pair of terminal flaps 10B longitudinally extending from the basic structure 10A.

Each of the barrier flaps 20 is formed using a sheet such as of a nonwoven fabric or plastic film, preferably using a liquid-impervious sheet and more preferably using a breathable liquid-impervious sheet 26. A length of the barrier flap 20 is not specified and, according to the one embodiment illustrated, the barrier flap 20 longitudinally extends along the side edge 17 of the pad 1 to the longitudinally opposite terminal edges 18 and the oblique edges 19. The sheet 26 forming the flap 20 is folded along the side edge 17 onto the front and rear surfaces of the pad 1. The portion of the sheet 26 extending on the front surface of the pad 1 is joined to the topsheet 22 at corner join zones 51 and an intermediate join zone 52 as indicated by hatches using hot melt adhesive 27 (See FIGS. 2 and 4) and the portion of the sheet 26 extending on the rear surface of the pad 1 is joined to the backsheet 23 at a join zone 28 indicated by hatches using hot melt adhesive 27 (See FIGS. 3 and 4). The portion of the sheet 26 extending on the front surface of the pad 1 has its distal marginal edge folded back along a longitudinally extending fold line 39 and joined to itself with its inner surface inside using hot melt adhesive 30A to form a free edge portion 40A of the leak-proof flap 20 presenting an annular cross-section.

The free edge portion 40A of the barrier flap 20 wraps a first elastic member 34 continuously or intermittently secured under a longitudinal tension to the inner surface of the free edge portion 40A over its full length using hot melt adhesive (not shown). While the first elastic member 34 may be laid immediately inside the fold line 39, preferably the first elastic member 34 is spaced inward, as illustrated, from the fold line 39 by a dimension P of 1 mm, preferably of 1–20 mm.

The sheet 26 are folded back along the side edge 17 of the pad 1 and put flat and joined to itself with interposition of hot melt adhesive 30B to form a free edge portion 40B of the side flap 10A.

The portions of the sheet 26 folded back along the side edge 17 of the pad 1 sandwich a second longitudinally extending elastic member 36 which is, in turn, continuously or intermittently bonded with a longitudinal tension to the inner surface of the sheet 26 using hot melt adhesive (not shown). Such second elastic member 36 is spaced from the side edge 17 by a dimension R of at least 1 mm, preferably of 1~20 mm. The second elastic member 36 is laid to confront the curved region 24D of the core 24 so that the portion of the side flap 10A extending outside the curved region 24D of the core 24 may be formed with gathers as the second elastic member 36 contracts.

Referring to FIG. 3, there are provided a pair of rectangular fasteners 31 on the rear side of the pad 1 immediately inside the longitudinally opposite terminal edges, respectively. The fasteners 31 serve for detachably fastening the pad 1 to the inner side of the diaper cover 2 and each of these fasteners 31 may be formed by suitable means such as one of a hook member and a loop member constituting together a mechanical fastening system or a strip of pressure-sensitive adhesive tape. The fasteners 31 extend transversely of the pad 1 and are attached to the backsheet 23 by means of hot melt adhesive or pressure-sensitive adhesive so that respective lateral ends of these fasteners 31 may lie adjacent the respective corners 21 of the pad 1.

As will be seen in FIG. 1, the pad 1 is curved and the first and second elastic members 34, 36 contract as the diaper cover 2 assembled with the pad 1 is put on a wearer's body and longitudinally curved. Contract of the first elastic members 34 causes the barrier flaps 20 to form gathers and at the same time to rise on their proximal edge portions defined by the respective intermediate bond zones 52 as indicated by two-dot-chain lines in FIG. 4. In this manner, the barrier flaps 20 form a pocket 20A opening inwardly of the pad 1. The free edge portions 40A of the barrier flaps 20 are placed against, for example, the inguinal region of the wearer. Contract of the second elastic members 36 generates gathers between the free edge portions 40B of the side flaps 10A and their proximal edge portions extending along the curved regions 24D of the core 24. These gathers are elastically placed against the wearer's skin, for example, around the legs.

The barrier flaps 20 as well as the side flaps 10A have their free edge portions 40A, 40B presenting the annular cross-sections. In addition, the first elastic members 34 are spaced from the fold lines 39 of the free edge portions 40A and the second elastic members 36 are also spaced from the side edges 17 substantially defining the fold lines of the free edge portions 40B. Consequently, the sheet 26 forming the flaps 20, 10A is freely deformed to round out or collapsed at the respective free edge portions 40A, 40B as indicated by single-dot-chain line in FIG. 4 as the flaps 20, 10A come in contact with the wearer's skin and thereby to prevent the first and second elastic members 34, 36 from cutting into the wearer's skin. The possibility that the first and second elastic members 34, 36 might cutting into the wearer's skin can be reliably avoided even if the pad 1 is put on the wearer's body somewhat incorrectly because the first and second elastic members 34, 36 are continuously or intermittently secured to the sheet 26 over their full lengths and therefore immovable relative to the sheet 20.

Figure 6:
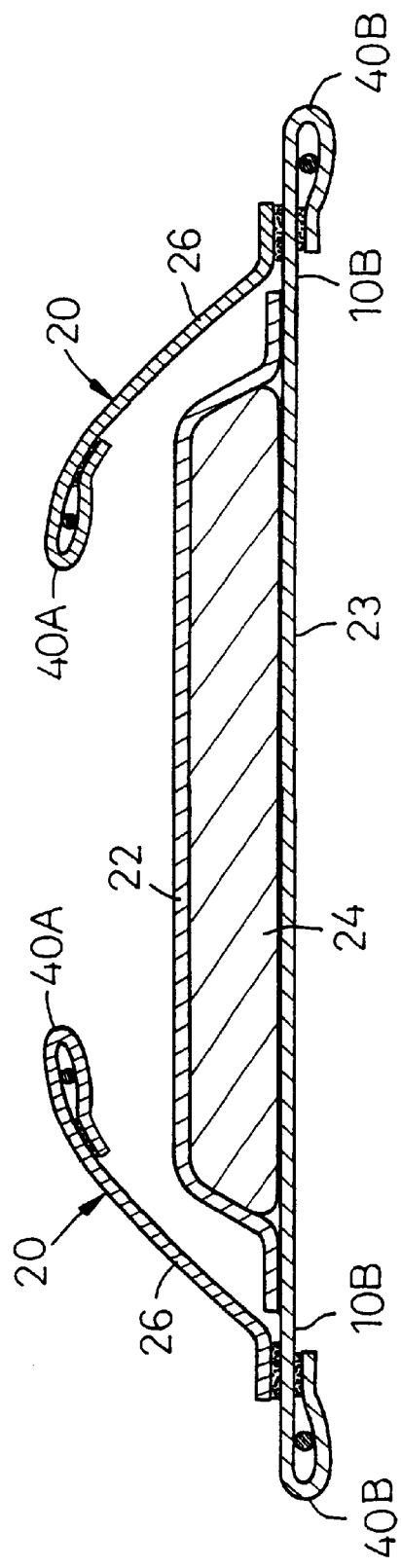
FIG. 6 is a view similar to FIG. 4 depicting an alternative embodiment of this invention.

FIG. 6 is a view similar to FIG. 4 depicting an alternative embodiment of this invention. This urine pad 1 differs from that of FIG. 4 in that the backsheet 23 laterally extends beyond the topsheet 22 to form the side flaps 10B and the sheets 26 are joined to the upper surfaces of respective side flaps 10B to form the barrier flaps 20. In this manner, it is possible without departing the scope and spirit of this invention to form the side flaps 10A and the barrier flaps 20 of the urine pad 1 by separate sheet materials so far as the flaps 10A, 20 have their free edge portions 40A, 40B presenting the annular cross-sections.

Exploitation of this invention is not limited to the absorbent sanitary article such as the urine pad 1 as has been described hereinabove. This invention can be exploited also in the form of the sanitary article having any one of the side flaps 10A and the barrier flaps 20. Furthermore, the idea of this invention is applicable also to at least one of the plural flaps included in the sanitary article. It should be noticed here that the barrier flaps 20 lying on the inner side of the article 1 are often formed by a nonwoven fabric having a relatively small basis weight while the side flaps 10A defining the outer periphery of the article 1 are often formed by sheet material having a relatively high rigidity. More specifically, either a plastic film having a high rigidity or a thick nonwoven fabric having a basis weight of 15~50 g/m$^2$ both rarely used as stock material for the topsheet is often used as the backsheet 23 or the sheet 26 forming the side flaps 10A. This invention may advantageously applied to the side flaps 10A comprising such material in order to improve a feeling to wear the sanitary article.

For exploitation of this invention, joining of the various members relying on hot melt adhesive may be also achieved using the other means such as heat-sealing technique. The disposable absorbent sanitary article according to this invention includes, in addition to the urine pad, various specific examples such as training pants, menstruation pads and panty liners. In these sanitary articles, positions as well as sizes of the respective pairs of flaps are not limited to those in the illustrated embodiment but may be selectively designed.

What is claimed is:

1. A disposable absorbent article comprising:

a first surface configured to face and contact a wearer's skin;

a second surface opposed to said first surface;

an absorbent element for absorbing and retaining body fluids, said absorbent element being positioned between said first and second surfaces; and a plurality of pairs of flaps configured to be elastically placed against the wearer's skin, each of said plurality of pairs of flaps having a transverse direction and a longitudinal direction orthogonal to said transverse direction and being formed from a sheet that extends outward from said absorbent element, each of said plurality of pairs of flaps being folded transversely so as to wrap around transverse edges of the absorbent article and be superimposed on transverse edge portions of both the first and second surfaces, each of said plurality of pairs of flaps further including an elastic member wrapped by said sheet in a tensioned state along said longitudinal direction, each of said plurality of pairs of flaps further having a proximal edge portion adjacent said absorbent element and an elastically stretchable free edge portion spaced apart from said absorbent element with said sheet being folded at the free edge portion about a fold line to provide a folded portion at said free edge portion that extends along said longitudinal direction, with said elastic members wrapped within the folded portions of said of the plurality of pairs of flaps and an unobstructed gap provided between the elastic members and fold line of each flap which unobstructed gaps allow the free edge portion of the flaps to collapse against the elastic members, said elastic member of each of said plurality of pairs of flaps being positioned at least 1 mm apart from a respective fold line thereof toward said proximal edge portion and bonded to the inner surface of said sheet.

2. The sanitary absorbent article according to claim 1, wherein each of said elastic members is spaced apart from an adjacent fold line by at least about 1 to 20 mm.

3. The absorbent article according to claim 1, wherein portions of said plurality of pairs of flaps extend laterally outward from said absorbent element and function as a pair of body fluid barrier flaps.

4. The absorbent article according to claim 1, wherein said sheet comprises a nonwoven fabric that has a basis of about 15 to 50 g/m$^2$.

5. The sanitary absorbent article according to claim 1, wherein said absorbent article comprises any one of a disposable diaper, a urine pad, training pants, a menstruation pad and a panty liner.

* * * * *